United States Patent [19]

Cullor

[11] Patent Number: 4,491,126
[45] Date of Patent: Jan. 1, 1985

[54] METHOD AND APPARATUS FOR MONITORING BODY PARTS OF ANIMALS

[75] Inventor: James S. Cullor, 128 Shasta Pl., Woodland, Calif. 95615

[73] Assignees: Wilbur D. Smith, Nevada, Mo.; James Cullor, Fort Scott, Kans.; James S. Cullor, Woodland, Calif.; Gary W. Cullor, Fort Scott, Kans.

[21] Appl. No.: 395,830

[22] Filed: Jan. 6, 1982

[51] Int. Cl.³ .................... A61B 19/00; A61M 25/00
[52] U.S. Cl. .................... 128/1 R; 604/49; 604/55; 604/175
[58] Field of Search .......... 604/29, 38, 49, 93, 604/151, 175, 247, 256, 281, 283; 128/19, 1 R; 605/55

[56] References Cited

U.S. PATENT DOCUMENTS

| | | | |
|---|---|---|---|
| 3,039,468 | 6/1962 | Price | 604/49 |
| 3,540,451 | 11/1970 | Zeman | 604/175 X |
| 3,633,585 | 1/1972 | McDonald, Jr. | 604/29 X |
| 4,193,392 | 3/1980 | Barnett | 128/1 R |
| 4,315,513 | 2/1982 | Nawash et al. | 604/38 X |
| 4,344,435 | 8/1982 | Aubin | 604/175 |
| 4,365,632 | 12/1982 | Kortum | 128/1 R |

Primary Examiner—C. Fred Rosenbaum
Assistant Examiner—Michelle N. Lester
Attorney, Agent, or Firm—Schmidt, Johnson, Hovey & Williams

[57] ABSTRACT

An improved method and apparatus is disclosed for adding fluids to, or removing fluids from, a body part or organ of an animal which minimizes animal trauma and permits rapid, easy, repeated fluid or low viscosity gels transfers. The apparatus includes a valve assembly having a tubular fluid-conveying element adapted for fixed connection to the animal, along with a fluid conduit connected between the valve element and a specific internal body part or organ, such as a cow's uterus. In use, a syringe is employed to introduce or remove fluids from the body part, through the valve assembly and connected conduit. The invention is especially adapted for introducing, recovering cell lines producing monoclonal antibodies or other biologically active products in large mammals, and facilitates monitoring of antibody production as well as administration of nutrients to enhance cell line growth.

3 Claims, 9 Drawing Figures

METHOD AND APPARATUS FOR MONITORING BODY PARTS OF ANIMALS

BACKGROUND OF THE INVENTION

1. Field of the Invention

The present invention is broadly concerned with a method and apparatus designed to greatly facilitate addition of fluids to, or removal of fluids from, an internal body organ or part of an animal. More particularly, it is concerned with such a method and apparatus which is especially suited for the large scale production of monoclonal antibodies in large mammals, and which permits repeated monitoring and/or nutritional enhancement of the in vivo monoclonal antibody production procedure.

2. Description of the Prior Art

When a foreign substance enters the body of a vertebrate animal or is injected into it, one aspect of the immune response is the secretion by plasma cells of antibodies. Quite apart from the natural function of antibodies in the animal's immune response, such antibodies have long been an important tool for investigators, who capitalize on their specificity to identify or label particular molecules or cells and to separate them from a mixture. The antibody response to a typical antigen is normally highly heterogeneous, and even the best of antisera are really heterogeneous mixtures of many different antibody molecules that vary in charge, size, and in such biologic properties as the ability to fix complement or to agglutinate or precipitate antigen. It is extremely difficult to separate the various antibodies in antisera, and therefore conventional antisera contain mixtures of antibodies, and such mixtures vary from animal to animal.

It is also known that malignant tumors of the immune system (called myelomas) are characterized by rapidly proliferating cells producing large amounts of abnormal immunoglobulines called myeloma proteins. A tumor itself is considered to be an immortal clone of cells descended from a single progenitor, and so myeloma cells can be cultured indefinitely, and all the immunoglobulines they secrete are identical in chemical structure. They are in effect monoclonal antibodies, but there is no way to know what antigen they are directed against, nor can one induce myelomas that produce antibody to a specific antigen. However, in recent years researchers have learned how to fuse myeloma cells of mice with lymphocytes from the spleen of mice immunized with a particular antigen. The resulting hybrid myeloma, or "hybridoma" cells express both the lymphocyte's property of specific antibody production and the immortal character of the myeloma cells. Such hybrid cells can be manipulated by the techniques applicable to animal cells in permanent culture. Individual hybrid cells can be cloned, and each clone produces large amounts of identical antibody to the single antigenic determinant. The individual clones can be maintained indefinitely, and at any time samples can be grown in culture or injected into animals for large scale production of monoclonal antibody. Highly specific monoclonal antibodies produced by this general method have proved to be a versatile tool in many areas of biological research and clinical medicine.

While the utility of specific monoclonal antibodies is manifest, a problem has arisen because of the difficulty of producing significant (e.g., liter) quantities of the antibodies. Obviously, the production of such antibodies in mice is not at all suited for large scale production. In response to this problem, it has been suggested to employ large mammals such as cattle or sheep for in vivo production of monoclonal antibodies. Indeed, a very recent breakthrough in this area has demonstrated the usefulness of this approach, particularly in the context of monoclonal antibody production in a cow's uterus. In such a procedure, the cells of hybridoma clones are introduced into the uterus of a cow in the early stages of gestation, and are allowed to multiply. After a suitable growth period, an extremely large quantity of monoclonal antibodies can be harvested from the uterus. While the above described technique shows considerable promise, a number of practical problems remain. For example, it is desirable to monitor the production of monoclonal antibodies in the cow's uterus, and the problems of obtaining samples of the uterine fluid on a frequent recurrent basis are formidable. The straightforward procedure of simply making a laparotomy incision in the cow's body, manipulation of the uterus, introducing or withdrawing materials, can create multiple insults to the cow, uterus and fetus, thus traumatizing the cow, uterus and fetus, which may lead to premature death, infection, or abortion of the fetus. By the same token, in order to enhance antibody production in the cow's uterus, it is oftentimes desirable to introduce nutrient fluids into the uterus. Here again, the conventional techniques for such introduction, if used repeatedly, can cause severe problems to the animal and uterine environment.

It will therefore be seen that there is a real and unsatisfied need in the art for a method and apparatus which permits easy, rapid addition of fluids to, or removal of fluids from, specific body parts or organs of animals, so as to facilitate the monitoring and production of monoclonal antibodies while at the same time avoiding repeated insults to the animal and other internal organs.

SUMMARY OF THE INVENTION

The problems outlined above are in large measure solved by the present invention which provides an apparatus for selectively transferring fluids to or from a specific body part or organ of an animal. Broadly speaking, the apparatus comprises a valve assembly of length to extend from the outer surface of the animal's skin into a body cavity of the animal. The valve assembly has an elongated, tubular, fluid-conveying element, along with means for retaining the element in place with the element passing through the animal's skin and the inner end of the element being in communication with the cavity of the animal's body. Valve means is operatively coupled with the element for normally blocking fluid flow, and includes structure for selective opening of the element to permit such fluid flow therethrough. The overall apparatus further includes an elongated fluid-conveying conduit designed for attachment to the inner end of the valve element and a specific internal body part or organ of the animal.

A method of periodically and selectively removing fluids from, or adding fluids to, an animal body part or organ is also within the ambit of the invention, and involves fixedly positioning the valve assembly element on the animal with the inner end of the assembly extending into a cavity of the animal's body, and with the tubular element being in communication with the cavity. A fluid-conveying conduit is operatively coupled to the element and the body part or organ (such as a cow's uterus). With the valve assembly and conduit thus in place, it is a simple matter to periodically and selectively withdraw fluids from, or add fluids to, the specific body part or organ by opening the valve assembly and passing fluid through the element and conduit.

DESCRIPTION OF THE PREFERRED EMBODIMENT

Figure 1:
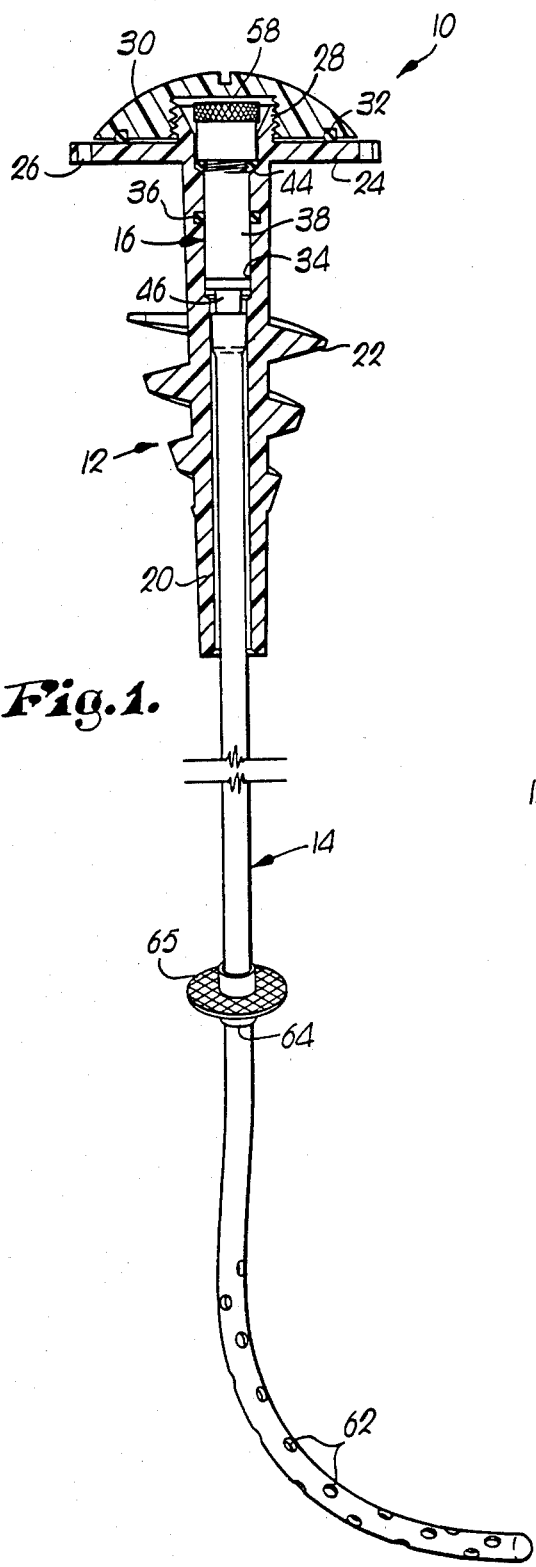
FIG. 1 is a fragmentary view in partial vertical section illustrating a fluid-conveying apparatus in accordance with the present invention.

Turning now to the drawings, the fluid-conveying apparatus 10 in accordance with the invention is illustrated in FIGS. 1-6. Broadly speaking, the apparatus 10 includes a valve assembly 12 along with an elongated conduit 14. The valve assembly 12 in turn includes an elongated, tubular, fluid-conveying element 16, as well as valving means 18 carried within the element 16.

In more detail, the valve assembly 12 preferably includes an elongated, slightly tapered, open ended outer tubular component 20 formed of an appropriate synthetic resin material and having an outwardly extending screw thread 22 formed thereon. The upper end of the component 20 is provided with an enlarged flange-type head 24 having a plurality of circumferentially spaced apertures 26 therethrough, as well as an upstanding, central, threaded annular connector 28. An outermost, rounded, removable synthetic resin cap 30 is threaded onto connector 28 as illustrated, and includes an O-ring seal 32 which abuts the upper surface of head 24 (see FIG. 1). The component 20 is configured to present a continuous, stepped, internal bore 34 along the length thereof and has an internal O-ring seal 36 spaced downwardly from head 24.

The tubular element 16 is situated within the upper, enlarged diameter portion of bore 34, and includes a synthetic resin tubular member 38 which is threaded at its upper end, the latter extending to a point adjacent surrounding connector 28. The inner surface of member 38 defines a fluid-conveying passage 40, and is configured to present an annular, obliquely oriented engagement surface 42 which is important for purposes to be made clear. Another seal 44 is disposed about the upper end of the member 38, and is situated within the upper end of bore 34 (see FIG. 2).

Figure 2:
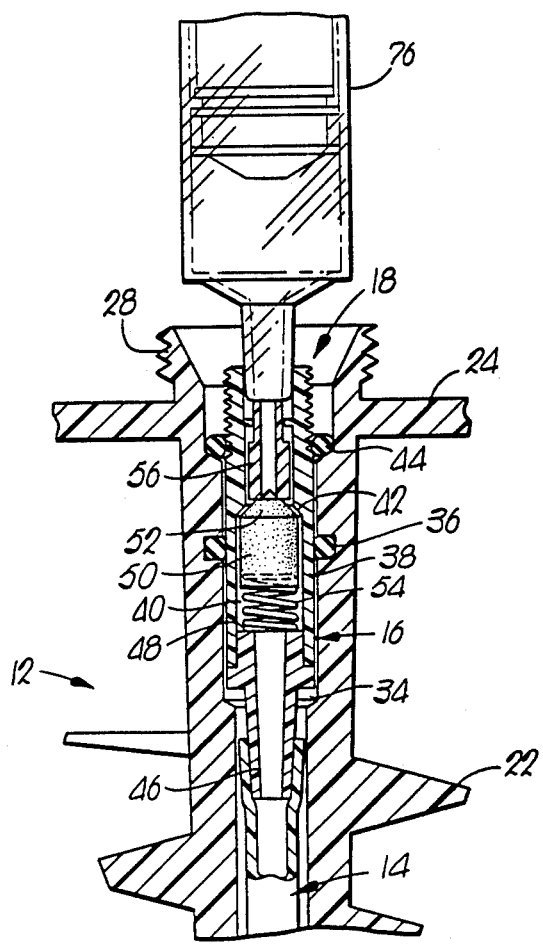
FIG. 2 is an enlarged, fragmentary view in partial vertical section illustrating the valve assembly of the overall apparatus, with a syringe positioned for operating the internal valve means thereof.
Figure 4:
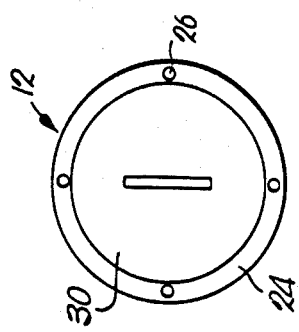
FIG. 4 is a top view of the assembly depicted in FIG. 3.
Figure 3:
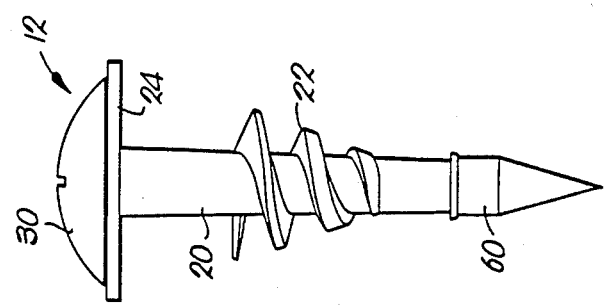
FIG. 3 is a side elevational view of the valve assembly prior to application thereof to an animal.

The tubular element 16 also includes a lowermost tabular part 46 which is received within the lower end of member 38 and presents an annular abutment surface 48. The lower end of part 46 is of frustoconical configuration as best seen in FIG. 2. In addition, it will be observed that the bore of part 46 is coaxial and in communication with the passage 40 of member 38.

Valving means 18 is situated to normally block flow of fluid through the element 16. In detail, the valving means 18 includes a shiftable plug 50 presenting a conical upper sealing surface 52 which is complemental with and adjacent engagement surface 42 of member 38. A helical spring 54 is situated between the underside of plug 50 and the abutment surface 48, and serves to bias plug 50 against engagement surface 42 for purposes of normally sealing the member 38, and thus overall tubular element 16, against fluid flow therethrough.

A tubular actuator 56 is positioned atop plug 52 and in engagement with the latter. The actuator 56 extends upwardly from the plug 50 and into the annular region defined by the threaded upper end of the member 38. It will be observed in this respect that the actuator 56 is centrally bored for passage of fluids.

Figure 5:
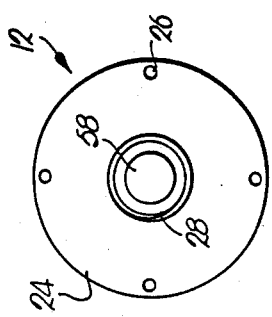
FIG. 5 is a top view, with the uppermost protective cap removed, of the assembly illustrated in FIG. 3.
Figure 6:
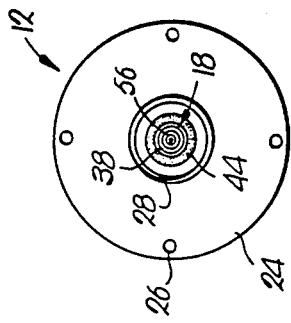
FIG. 6 is a view similar to that of FIG. 5, but illustrates the inner protective cap removed to expose the internal valve means.

Referring to FIGS. 1 and 5, it will be seen that an inner cap 58 is advantageously applied to the upper threaded end of member 38, in order to further seal the internal valving means 18 when the latter is not in use. In addition (see FIG. 3), a removable insertion tip 60 is affixed to the lower open end of the tubular component 20.

The conduit 14 is advantageously in the form of plastic tubing which is dimensioned to receive and tightly engage the lower end of part 46 (see FIGS. 1 and 2), and thus be operatively connected to the tubular element 16. The end of conduit 14 remote from the valve assembly 12 is provided with a plurality of fluid flow apertures 62 through the defining wall thereof. In addition, an attachment collar 64 is situated on conduit 14 intermediate the ends thereof, and has an annular, outwardly extending cloth or synthetic resin attachment flange 65.

Figure 9:
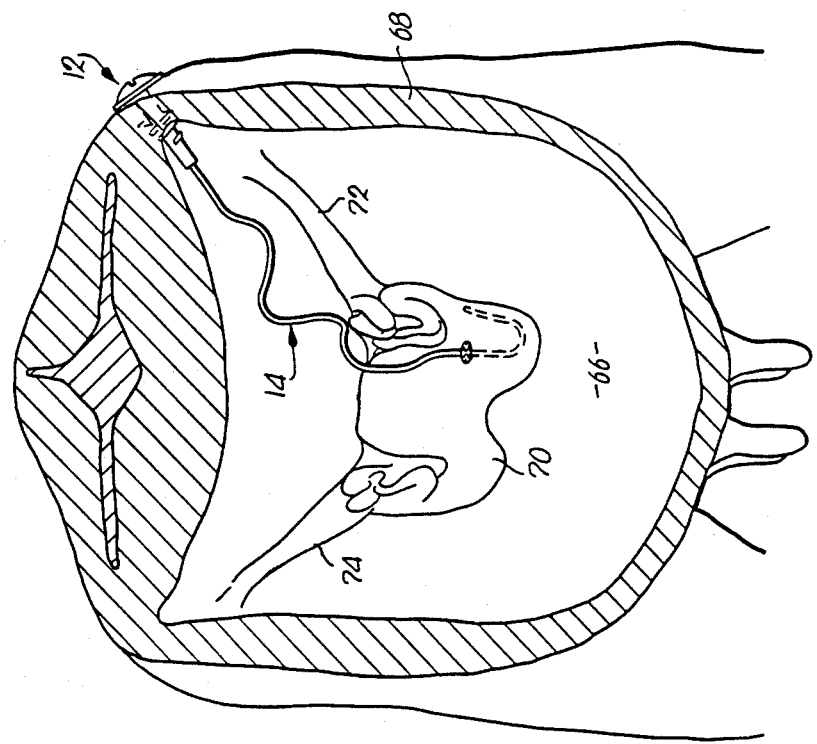
FIG. 9 is a view similar to that of FIG. 8, but illustrates the completed apparatus in place with the fluid-conveying conduit operatively connected to the inner end of the valve assembly.
Figure 8:
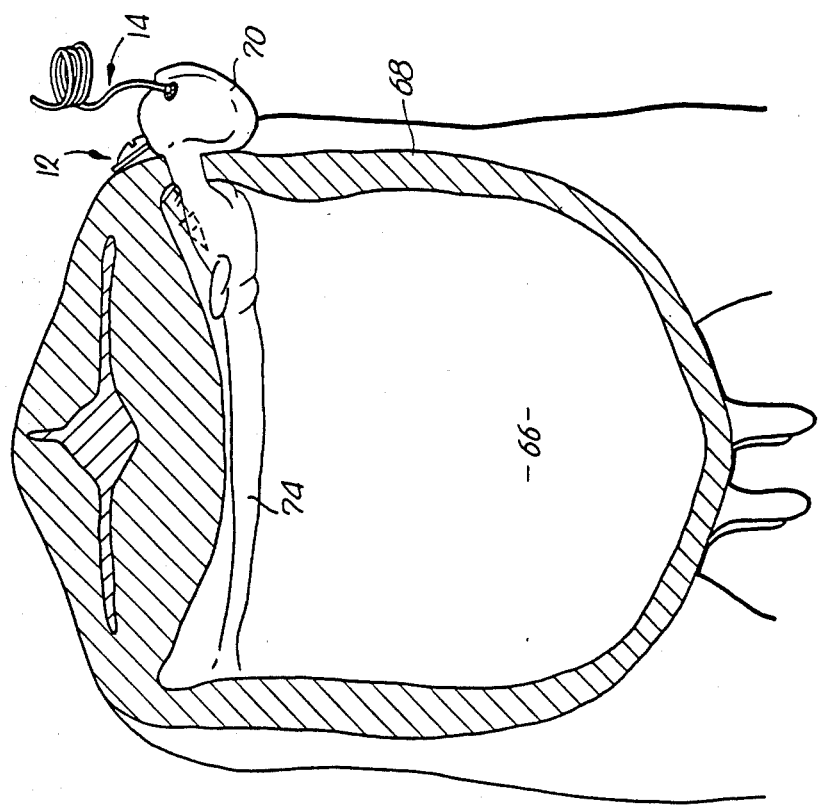
FIG. 8 is a view similar to that of FIG. 7, but illustrates the procedure wherein a fluid-conveying conduit is inserted into and connected to the cow's uterus.
Figure 7:
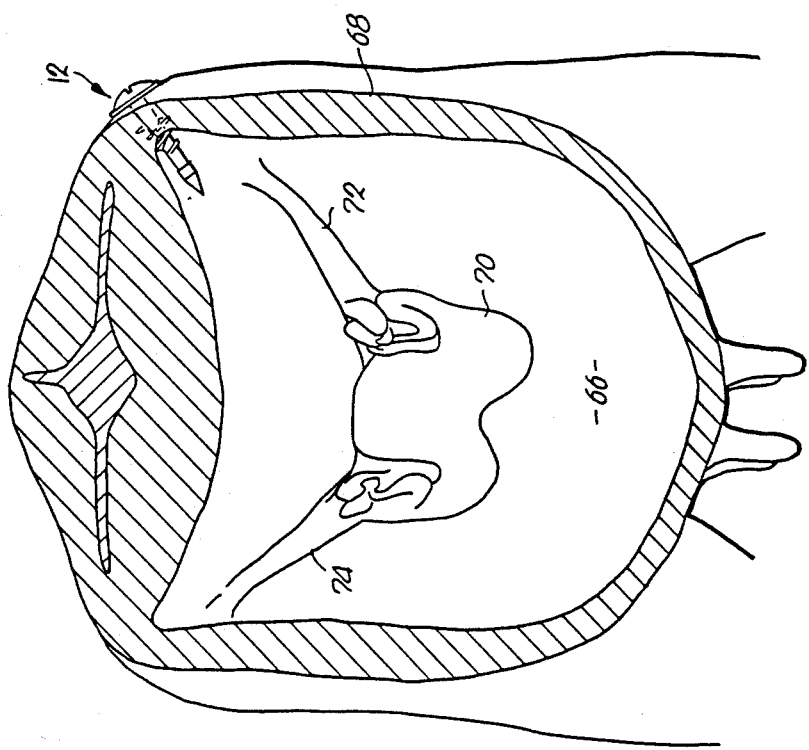
FIG. 7 is a schematic, sectional view illustrating the abdominal cavity of a cow, along with the cow's uterus, and with the valve assembly of the invention inserted in place on the cow extending into the abdominal cavity.

FIGS. 7-9 depict an illustrative installation of the apparatus 10 of the invention. In the Figures, the abdominal cavity 66 of a cow 68 is shown. The uterus 70, supported by ligaments 72, 74 is likewise depicted.

Installation of device 10 on cow 68 may involve initially tranquilizing the cow and administering a local anesthesia at the selected laparotomy site(s), typically left or right paralumbar fossa. A skin incision is next made, typically a caudal and dorsal to laparotomy incision. The valve assembly 12 is next inserted into the incision using a rotating action so that the component 20 is in effect screwed into and through the abdominal cavity wall until the inner end of the valve assembly is disposed within cavity 66 (see FIG. 7). Tack down sutures of non-absorbable suture material are next installed through the apertures 26 in head 24, in order to fixedly position the component 20, and thereby the element 16 and valving means 18 carried therein, on the cow 68.

The cow's uterus is next grasped and pulled outside of cavity 66 (see FIG. 8). If necessary, another incision is made in the abdominal cavity wall to permit such manipulation of the uterus. In any event, one may choose to make a small (1 cm.) incision through the uterine wall, and the fenestrated conduit 14 is inserted into the uterus; sufficient length is allowed within the uterus for uterine growth and descent into the abdominal cavity as gestation proceeds. A so-called "purse-string" suture is then placed through the uterine wall and the flange 65, using suture material. The incision and suture are then checked for fluid leakage, and the collar 64 is secured to conduit 14 by gluing.

The uterus 70 is next replaced in its normal position, making certain that sufficient excess tubing is present to connect with the valve assembly 12 and allow for normal animal movement and fetal growth. The penetrating point or tip 60 is next removed, and the free end of conduit 14 is operatively coupled with the valve assembly 12 by passing the end of the conduit into component 20 and over part 46 (see FIG. 2). The caps 30 and 58 are then removed, and a syringe 76, with needle removed, is used to aspirate the apparatus and check for fluid flow. The caps 30, 58 are next replaced, and the laparotomy incision is closed.

In a typical procedure for the production of monoclonal antibodies, inoculation of the cow's uterus or fetus may occur 5–7 days after installation of apparatus 10, assuming that the cow's systemic inflammatory response has decreased and after it has been determined that the pregnancy is being maintained. Such inoculation would include introduction of conditioning reagents (e.g., pristane albumins and the like) in uterine fluids, followed by inoculation of the cell lines. Incubation varies with the specific cell line selected, and in general the uterine fluids are monitored periodically using apparatus 10. When it is desired to harvest the cell line and its products, such may be accomplished through the use of device 10, through cesarean section, or by sacrificing the cow. Typical enrichment constituents added to the uterine fluid during the incubation sequence would include, inter alia, amino acids, bovine serum albumin, vitamins, inorganic salts, and suspension mediums. More specifically, amino acids such as L-Glutamine, L-Argine, L-Cystine, and L-Histadine $HCl \cdot H_2O$ may be added. Vitamin addition may include D-Calcium Pantothenate, Thiamine HCl, Choline Chloride and Riboflavin. Inorganic salts may include KCl, $NaHCO_3$, $NaH_2PO_4 \cdot H_2O$, and $CaCL_2 \cdot 2H_2O$. Finally, suspension mediums such as Dextrose, Phenol Red, $MgCL_2 \cdot 6H_2O$, and NaCl, KCl may be included.

When it is desired to utilize apparatus 10 either for introduction of fluids into, or removal of fluids from, the cow's uterus, the following procedure obtains. First, the caps 30, 58 are removed, and a syringe 76 (see FIG. 2), with needle removed, is pressed downwardly into the upper end of member 38 until the actuator 56 is encountered. The syringe is thereupon pressed inwardly with the effect that the plug 50, and particularly surface 52 thereof, is shifted away from mating surface 42 against the bias of spring 54. When this occurs, it will be seen that a fluid flow path is established through tubular actuator 56, passage 40, the bore of part 46, and conduit 14. Thus, fluids can be administered through apparatus 10 into uterus 70 simply by manipulating syringe 76 in the usual injection manner. By the same token, fluids can be withdrawn from the uterus by the opposite manipulation of syringe 76, as those skilled in the art will readily appreciate.

It should also be understood that while the apparatus and method have been illustrated in connection with a cow's uterus, the invention is not so limited. For example, the apparatus can be used with virtually any large mammal such as sheep, goats or cattle. In addition, other body parts or organs can be connected to the apparatus hereof, e.g., the bladder, intestine or rumen compartments. Finally, while the methods hereof are particularly useful in connection with production of monoclonal antibodies, the invention can also find significant utility in the inoculation, enrichment, monitoring and/or harvesting of virtually any cell line producing a secretory product.

I claim:

1. A method of growing cells in and harvesting grown cells or the secretory products thereof from the uterus of a living animal, said method comprising the steps of:

providing a tubular, fluid-conveying element;

operatively securing said element to said animal's body with the outer end of the element adjacent the exterior surface of the animal's skin;

operatively coupling an elongated, flexible, fluid-conveying conduit to, respectively, said element and said uterus, said coupling step including the steps of initially moving said uterus to a convenient working position, making an incision in the wall of said uterus and inserting the inner end of said conduit into said uterus until an elongated, flexible innermost portion of the conduit lies within the confines of said uterus, said conduit being of a length greater than the shortest distance between said element and said incision such that a portion of the conduit lies within the abdominal cavity of said animal exteriorly of said uterus for, in conjunction with the flexiblity of the conduit, permitting and accommodating natural uterine growth and movement as gestation proceeds;

physically attaching and interlocking said inner end of said conduit to said wall of said uterus, with said elongated, flexible innermost portion lying within the confines of said uterus, for preventing leakage of fluid from said uterus, said attaching and interlocking step comprising the steps of providing a radially outwardly extending, suturable collar affixed to said conduit intermediate the ends thereof, and suturing said collar to the wall of said uterus;

subsequent to said attaching and interlocking step repositioning said uterus at the normal position thereof within said adominal cavity;

placing a cell line in said uterus;

thereafter incubating the cell line in said uterus and periodically and selectively withdrawing fluid from, or adding fluid to, said uterus containing said cell line by conveying said fluid through said conduit and element; and harvesting grown cells or the secretory products of said cells from said uterus.

2. The method of claim 2, including the steps of initially positioning said uterus at least partially outside of the abdominal cavity of said animal.

3. The method of claim 2, said cell line being capable of producing monoclonal antibodies.

* * * * *